United States Patent [19]

Burns

[11] Patent Number: 6,028,057
[45] Date of Patent: Feb. 22, 2000

[54] REGULATION OF ESTRUS AND OVULATION IN GILTS

[75] Inventor: Patrick J. Burns, Lexington, Ky.

[73] Assignee: Thorn BioScience, LLC, Lexington, Ky.

[21] Appl. No.: 09/026,463

[22] Filed: Feb. 19, 1998

[51] Int. Cl.$^7$ .............................. A61K 38/00; C07K 5/00; C07K 7/00
[52] U.S. Cl. .............................................. 514/12; 530/324
[58] Field of Search ................................ 514/12; 530/324

[56] References Cited

U.S. PATENT DOCUMENTS

| | | |
|---|---|---|
| 3,860,701 | 1/1975 | Short . |
| 3,991,750 | 11/1976 | Vickery . |
| 4,732,763 | 3/1988 | Beck et al. . |
| 4,756,907 | 7/1988 | Beck et al. . |
| 4,975,280 | 12/1990 | Schacht et al. . |
| 5,418,228 | 5/1995 | Bennink . |
| 5,434,146 | 7/1995 | Labrie et al. . |
| 5,512,303 | 4/1996 | Garza Flores et al. . |
| 5,585,370 | 12/1996 | Casper . |
| 5,605,702 | 2/1997 | Teillaud et al. . |
| 5,633,014 | 5/1997 | Flores et al. ............................ 424/489 |
| 5,650,173 | 7/1997 | Ramstack et al. . |
| 5,686,097 | 11/1997 | Taskovich et al. . |
| 5,747,058 | 5/1998 | Tipton et al. . |

FOREIGN PATENT DOCUMENTS

| | | |
|---|---|---|
| 2 166 951 | 5/1986 | United Kingdom . |
| 9737642 | 10/1997 | WIPO .............................. A61K 9/48 |
| WO 98/53837 | 12/1998 | WIPO . |

OTHER PUBLICATIONS

Fleury et al., J. Equine Vet. Sci., 13(9), pp. 525–528, (1993).

Pusateri et al., Biol. Reproduction, 55 pp 582–89, 1996.

Burns, et al., "Effects of Daily Administration of Estradiol–17β on Follicular Growth, Ovulation, and Plasma Hormones in Mares," *Biology of Reproduction* 24: 1026–1031 (1981).

Cook, et al., "Effects of Exogenous Estradiol Treatment in Cyclic Mares Following PGF$_{2\alpha}$ Induced Luteal Regression," *Proceedings of the 13$^{th}$ Equine and Physiology Symposium*, pp. 370–374.

Estill, et al., "Estrus Synchronization of Gilts Using Steroid–containing Implants and a PGF$_{2\alpha}$ Analogue," (available, but not presented, at the) *Society for Theriogenology, Proceedings for Annual Meeting*, Sep. 1997).

Kraeling, et al., "Susceptibility of the Pig Corpus Luteum to PGF$_{2\alpha}$ at Various Stages of Pregnancy," *Abstracts of 69$^{th}$ Ann. Mtg. Am. Soc. Anim. Sci.*, (Madison, WI 1977).

Van Der Muelen, et al., "Effect of intra–uterine oestradiol–17β administration of inter–oestrus interval in the pig," *Animal Reproduction Science* 24: 305–313 (1991).

PROKOFEVA, "Composition for Oestrus Cycle Control in Sows—Containing Hydroxy–progesterone Caproate, Oestradiol Valerate, Oil, and Benzyl Benzoate to Improve Heat Synchronisation" *Derwent Publications Ltd.*, SU–549118 (abstract), Jun. 23, 1977.

Britt, et al., "Induction of fertile estrus in prepuberal gilts by treatment with a combination of pregnant mare's serum gonadotrophin and human chorionic gonadotropin," *J. Anim. Sci.* 67:1148–53 (1989).

Burns, et al., "Evaluation of biodegradable microspheres for the controlled release of progesterone and estrodiol in an ovulation control program for cycling mares," *J. Equine Vet. Sci.* 13(9):521–24 (1993).

Doubrow, ed., "Microcapsules and Nanoparticles in Medicine and Pharmacy," (CRC Press, Boca Raton 1992) (Table of Contents Only).

Flowers, et al., "Reproduction Performance and Estimates of Labor Requirements Associated with Combination of Artificial Insemination and Natural Service in Swine," *J. Anim. Sci.* 70:615–21 (1992).

Geisert, et al., "Length of pseudopregnancy and pattern of uterine protein release as influenced by time and duration of estrogen administration in the pig," *J. Reprod. Fert.* 79:163–72 (1987).

Guthrie, et al., "Treatment of pregnant gilts with a prostaglandin analogue, Cloprostenol, to control estrus and fertility," *J. Reprod. Fert.* 52:271–73 (1978).

Guthrie, et al., "Changes in plasma estrogen, luteinizing hormone, follicle–stimulating hormone and 13,14–dihydro–15–keto–prostaglandin $F_2\alpha$ during blockade of luteolysis in pigs after human chorionic gonadotropin treatment," *J. Anim. Sci.* 57:993–1000 (1983).

Howard, et al., "Prostaglandin $F_2\alpha$ causes regression of an hCG–induced corpus luteum before Day 5 of its lifespan in cattle," *J. Reprod. Fert.* 90:245–53 (1990).

LaForest, et al., "Effect of topical application of estradiol–17β and $PGE_2$ on PGE–binding sites in the endometrium," *Reprod. Nutr. DEv.* 32(2):93–104 (1992).

Pusateri, et al., "Maternal Recognition of Pregnancy in Swine. I. Minimal Requirement for Exogenous Estradiol–17β to induce Either Short of Long Pseudopregnancy in Cycling Gilts," *Biol. Reproduction* 55:582–89 (1996).

Sheffield, et al., "Effect of estradiol and relaxin on collagen and non–collagen protein synthesis by mammary fibroblasts," *Life Sci.* 35:(22):2199–203 (1984).

Stevenson, et al., "Role of the Ovary in Controlling Luteinizing, Hormone Follicle Stimulating Hormone, and Prolactin Secretion During and After Lactation in Pigs," *Biol. Reproduction* 24:341–53 (1981).

*Primary Examiner*—Avis M. Davenport
*Attorney, Agent, or Firm*—Arnall Golden & Gregory, LLP

[57] ABSTRACT

Controlled release compositions and methods for inducing pseudopregnancy in gilts and sows are disclosed. In the preferred embodiment, the formulation includes polylactide microspheres releasing estradiol 17β at physiologically useful levels over a period of time between five and thirty days. Following induction of pseudopregnancy, the pseudopregnancy can be terminated and estrus induced by administration of a compound such as PGF2α. The advantages of inducing pseudopregnancy followed by induction of estrus are that the breeding patterns of large numbers of gilts and sows can be controlled.

24 Claims, 1 Drawing Sheet

REGULATION OF ESTRUS AND OVULATION IN GILTS

This invention is in the area of animal husbandry, in particular, controlled release formulations for the regulation of estrus and ovulation in gilts.

BACKGROUND OF THE INVENTION

In nature, gilts (young female pigs that have not yet given birth to a litter of pigs) normally reach puberty between the ages of 150 and 250 days. Once they reach puberty, they have a regularly recurrent period of ovulation and sexual excitement, known as "estrus" or "heat." Gilts are most likely to ovulate and conceive when they are in heat.

Gilts and sows normally do not have synchronous heats (estrus), and accordingly, do not all conceive at the same time. Young gilts also have a tendency to produce smaller and lighter litters as compared to sows.

A major goal of commercial swine production is to maximize reproductive efficiency, especially among gilts. Increased reproductive efficiency offers producers substantial opportunities to reduce production costs and enhance profitability. Efforts are being made to increase reproductive efficiency by breeding gilts at earlier ages, synchronizing estrus among the gilts, impregnating gilts using artificial insemination (AI) and increasing the litter size and increasing the birth and weaning weight of the litters.

Gilts can be bred at earlier ages by chemically inducing puberty. One means to chemically induce puberty is by administration of a single injection of PG600™ (pregnant mare's serum gonadotrophin and human chorionic gonadotropin). Gilts typically show estrus between three and six days after treatment, while between 90 and 95% of the gilts ovulate even if they do not show estrus. The estrual response rate can be enhanced when gilts are given daily boar stimulation by direct physical contact beginning at the time of PG600™ administration.

The litter size of gilts bred at their first chemically induced estrus is comparable to the litter size in gilts bred at their first natural estrus. However, larger litter sizes can be obtained by waiting until the second or third estrus. A major problem associated with waiting for the second or third estrus is that the estrus is no longer closely synchronized.

There are no products currently approved in the United States that are effective at regulating estrus once gilts have started to cycle so that estrus synchronization during the more productive second or third estrus cycles is presently not possible. Estrus regulation and scheduled breedings are done using alternative management techniques, keeping large pools of gilts so that a fixed number will always be in heat or allowing nature to take its course. These techniques, however, are not efficient.

The most common alternative management technique is to synchronize estrus in groups of gilts by first mating the gilts and then administering Prostaglandin F2α (PGF2α) to induce "synchronous abortion" as soon as two to three weeks, and up to eight to ten weeks after the end of the mating period. Aborted gilts show a normal heat and normal fertility if abortion is induced during the first 40 to 50 days after mating. Gilts that have experienced an incomplete pregnancy tend to have larger litters than gilts bred at first or second estrus. This method of synchronizing estrus is presently used in some large swine operations, but it requires extra boars and extra boar housing. In addition, aborted conceptuses are unsanitary and may cause gilts to develop endometriosis after aborting.

There is still a heavy reliance on daily heat detection of individual animals for timing of AI or breeding, and gilts and sows are still bred based on spontaneous estrus cycles. Approximately half of the labor in swine breeding facilities is devoted to detection of heat in breeding gilts or sows. Gilts or sows must be checked at least once daily in order to breed at the correct time, and if AI is used it may be necessary to check heat twice daily to achieve the best results. Rigorous heat detection is necessary because it is difficult to predict the day of heat for any cyclic gilt or open sow, even with good heat detection records. Gilts often stay in the gilt pool for three or four cycles before they are first detected in heat or detected at the right time to fit a breeding group.

Methods to synchronize estrus and increase weaned litter weights in gilts would significantly improve the efficiency of swine production. Recent efforts have focused on the induction of estrus by first inducing pseudopregnancy in large numbers of animals and then inducing estrus in the animals. Pseudopregnancy is a condition resembling pregnancy that occurs in some mammals after infertile copulation. In a pseudopregnancy, physical symptoms of pregnancy, such as absence of sexual receptivity, weight gain and mammary development are manifested without conception.

Pseudopregnancy can be induced using existing or emerging commercial pharmaceutical products. Pseudopregnancy has been induced in cyclic gilts by giving estrogen for between four and eight days beginning on day 11 after heat (Geisert et al., "Length of pseudopregnancy and pattern of uterine protein release as influenced by time and duration of estrogen administration in the pig," *J. Reprod. Fert.* 79:163 (1987) and Pusateri, et al. "Maternal recognition of pregnancy in swine I: Minimal requirements for exogenous estradiol-17β to induce short or long pseudopregnancy in cycling gilts," *Biol. Reprod.* 55: 582–589 (1996)). The compounds are typically administered by injection on a daily basis.

Pseudopregnant gilts maintain their corpus luteum (CL) for approximately 60 days and therefore can be induced to show heat "on demand" by treating with PGF2α during the pseudopregnancy (Geisert et al., (1987)). Heat usually occurs 3 to 6 days after PGF2α treatment in pseudopregnant gilts.

Daily injections or injected implants that have to be removed are impractical. It would be advantageous to provide a method for controlling the reproductive pathway for swine, especially gilts, that does not involve daily injections or the use of non biodegradable injected implants that need to be removed at the end of treatment.

It is therefore an object of the present invention to provide a method for controlling the reproductive pathway for swine, especially gilts, that does not involve daily injections or implants which have to be removed at the end of treatment.

It is another object of the present invention to provide a formulation for controlling the reproductive pathway of swine that uses a naturally-occurring estrogen or esters thereof that meets FDA approval.

SUMMARY OF THE INVENTION

Controlled release compositions and methods of use thereof are provided for regulating estrus and ovulation in gilts and sows. The methods involve administering a controlled release composition to the animals that induces pseudopregnancy, and then administering a composition to the animals which terminates the pseudopregnancy and induces estrus and luteolysis. One can manage the reproductive cycle of large numbers of gilts and sows by simultaneously inducing pseudopregnancy and then estrus in the animals.

The controlled release composition is preferably a microparticle formulation. The microparticles preferably include a biodegradable, biocompatible polymer such as polylactide that degrades by hydrolysis. In addition to microparticle systems, other controlled-release injectable or implantable formulations suitable for delivering a compound which induces pseudopregnancy can be used. Both degradable and non-degradable excipients can be used in the formulation of injectable or implantable controlled-release formulations, although degradable excipients are preferred.

Suitable compounds for inducing pseudopregnancy include estrogen and estrogen mimics. Suitable estrogens which can be used include any of those conventionally available, including natural and synthetic estrogens. Preferably, the estrogen is estradiol 17β, a naturally-occurring steroid. In a preferred embodiment, the methods involve administering a single injection controlled release microsphere formulation containing the naturally-occurring steroid estradiol 17β by intramuscular injection.

Suitable compounds for terminating the pseudopregnancy and inducing estrus include PGF2α and its commercially available analogs, including dinotrost tromethamine, fenprostelene, α-prosonol, cloprostonol, fluprostenol sodium, luprosiol sodium and prostelene. Preferably, the compound is PGF2α, dinotrost tromethamine, or fenprostelene, which are administered in a single injection. Preferably, the methods involve administration of Lutalyse™ (dinotrost tromethamine, 10 mg) (Pharmacia-Upjohn™) to induce a controlled estrus in the pseudopregnant gilts.

DETAILED DESCRIPTION OF THE INVENTION

Figure 1:
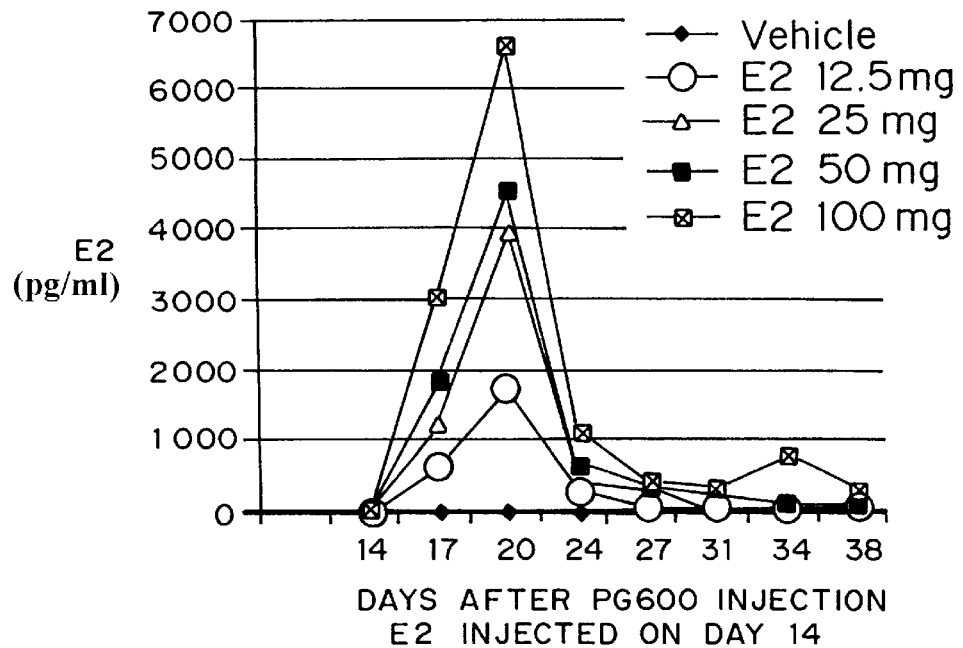
FIG. 1 is a graph showing the estradiol (E2) levels (pg/ml) in treated gilts. Filled diamonds represent vehicle. Circles represent treatment with 12.5 mg of estradiol. Triangles represent treatment with 25 mg of estradiol. Squares represent treatment with 50 mg of estradiol. Xs represent treatment with 100 mg of estradiol.

Compositions and methods are provided for regulating estrus and ovulation in gilts and sows. The compositions and methods allow the control of estrus and ovulation in gilts with sufficient precision that artificial insemination (AI) by appointment can be used routinely in commercial swine units.

The methods involve administering a controlled release composition to the animals that induces pseudopregnancy, and then administering a composition to the animals which terminates the pseudopregnancy and induces estrus and luteolysis. The controlled release composition is preferably a microparticle formulation formed of biodegradable polymers.

Animals and Formulations

A. Animals

Any fertile gilt or sow can be treated with the compositions and methods described herein. In a preferred embodiment, gilts are treated which, while pre-pubertal and between 160 and 200 days old, were treated with PG 600™ (Intervet Inc. Millsboro Del.) to induce puberty, and have responded to treatment with PG 600™ with a normal estrus between three and six days following treatment.

It is preferred to use these gilts because it allows for maximum efficiency in swine production. The gilts will have had their puberty induced chemically, their pseudopregnancy induced chemically, their estrus induced chemically, and can be artificially inseminated. This allows maximum automation and control of the swine reproductive cycle. However, gilts other than those whose puberty was induced chemically will respond to this treatment.

B. Compounds Useful for Inducing Pseudopregnancy

Suitable compounds for inducing pseudopregnancy include estrogens and estrogen mimics. Suitable estrogens which can be used include any of those conventionally available, including natural and synthetic estrogens. Suitable synthetic estrogens include those described in the 1993 Sigma Chemical Company Catalog, on pages 398–402, the contents of which are hereby incorporated by reference. Examples include 17 α-estradiol, mono and diesters of estradiol such as estradiol 17-acetate, estradiol 3,17-diacetate, estradiol-3-benzoate, and estradiol 17-undecanoate, mono and diethers of estradiol, alkyl derivatives at the 17 position of estradiol such as ethinyl estradiol and ethinyloestradiol 3-isopropylsulfonate, methyloestradiol, quenistrol, mestranol, and mixtures thereof. Suitable natural estrogens include conjugated equine estrogens, 17β-estradiol, estradiol valerate, estrone, piperazine estrone sulfate, estriol, estriol succinate and polyestrol phosphate. Preferably, the compound is estradiol 17β.

C. Controlled Release Formulations

Formulations should preferably release physiological levels of the compound used to induce pseudopregnancy over a period of between 5 and 30 days, preferably between 15 and 30 days, and more preferably, between 25 and 30 days.

Microparticles

As used herein, the term "microparticles" includes microspheres and microcapsules. The microparticles preferably are biodegradable and biocompatible, and optionally are capable of biodegrading at a controlled rate for delivery of a compound which induces pseudopregnancy. The particles can be made of a variety of polymeric and non-polymeric materials.

Materials Useful for Preparing the Microparticles

The microparticles can include any biocompatible, and preferably biodegradable polymer, copolymer, or blend. Suitable polymers include polyhydroxy acids, polyorthoesters, polylactones, polycarbonates, polyphosphazenes, polysaccharides, proteins, polyanhydrides, copolymers thereof and blends thereof. Suitable poly(hydroxy acids) include polyglycolic acid (PGA), polylactic acid (PLA), and copolymers thereof. Preferably, the microparticles include poly(D,L-lactic acid) and/or poly(D,L-lactic-co-glycolic acid) ("PLGA"). The preferred material is polylactide.

Particles with degradation and release times ranging from days to months can be designed and fabricated, based on factors such as the materials used to prepare the microparticles. Preferred release times are between approximately five and 30 days.

It is preferred that the compound which induces pseudopregnancy, preferably estradiol 17-β, be released at physiological levels over a period of weeks, most preferably, between twenty five and thirty days, so that the steroid is present during the initial four to eleven day window that occurs between nine and twenty days after the previous estrus which is required to induce pseudopregnancy in gilts.

Methods for Microparticle preparation

The microparticles, including microspheres and microcapsules, can be prepared using any method that does not destroy the activity of the compound used to induce pseudopregnancy. Microparticles may be prepared using single and double emulsion solvent evaporation, spray drying, solvent extraction, solvent evaporation, phase separation, simple and complex coacervation, interfacial polymerization, and other methods well known to those of ordinary skill in the art.

Methods developed for making microspheres for drug delivery are described in the literature, for example, as described in Doubrow, M., Ed., "Microcapsules and Nanoparticles in Medicine and Pharmacy," CRC Press, Boca Raton, 1992. See also, U.S. Pat. No. 5,407,609 to Tice et al., and U.S. Pat. No. 5,654,008 to Herbert et al., the teachings of which are incorporated herein, for methods of making microspheres.

Other Controlled Release Formulations

In addition to microparticle systems, other controlled-release injectable or implantable formulations suitable for delivering a compound which induces pseudopregnancy can be used. Both degradable and non-degradable excipients can be used in the formulation of injectable or implantable controlled-release formulations, although degradable excipients are preferred.

Examples of injectable formulations include typical depot formulations prepared with oily and waxy excipients (e.g. similar to Depot Provera™) and in situ gelling systems such as those prepared using sucrose acetate isobutyrate or biodegradable polymers.

Examples of implantable formulations include compressed tablet formulations such as those used for controlled release of growth promoters in cattle (e.g. Synovex™), and Compudose™ (a silicone rubber core coated with a thin layer of medicated silicone rubber containing estradiol). In one embodiment, biodegradable gels and/or implants can be used.

In addition to implantable formulations, various formulations which are easily inserted into and removed from the animal, for example, vaginal or cervical rings, sponges, for example, prepared from polyurethane, and intravaginal implants, can also be used.

Intravaginal implants can be used which are similar to CIDR (controlled internal drug release) currently used, for example, to administer progesterone intravaginally in cattle and sheep. Another type of implant is known as PRID (progesterone releasing intravaginal device) which includes stainless steel coils coated with silicone rubber containing progesterone, and which optionally includes a gelatin capsule containing estradiol.

Rods prepared by incorporating the active into a polymeric excipient can also be used. Suitable rods can be prepared using a variety of processes including the filling of the active compound into tubes formed from a rate-controlling membrane polymer or compounding the active compound with an excipient following by extrusion or molding to form the finished implant.

Suitable formulations can be developed by those skilled in the art using any of the approaches described above and typical pharmaceutical excipients.

D. Compounds Useful for Terminating Pseudopregnancy and Inducing Estrus

Suitable compounds for terminating the pseudopregnancy and inducing estrus include PGF2α, dinoprost tromethamine, fenprostelene, α-prosonol, cloprostonol, fluprostenol sodium, luprosiol sodium and prostelene. Preferably, the compound is PGF2α, dinoprost tromethamine or fenprostelene. Preferably, the methods involve administration of Lutalyse™ in a single injection.

Methods of Treatment

A. Inducement of Pseudopregnancy

There is a relatively narrow window of time in which pseudopregnancy can be induced in swine. This window is a four to eleven day period which occurs between nine and twenty days after the previous estrus. Pseudopregnancy is induced in the animals by administering an effective amount of a controlled-release formulation of a compound which induces pseudopregnancy, for example, an estrogen or estrogen mimic. The release of the compound preferably occurs over a period of between five and thirty days, more preferably between 15 and 30 days, and most preferably, between 25 and 30 days.

When the compound to be administered is estradiol 17β (the same estrogen that gilts produce), a suitable dosage range is between 10 and 100 mg per animal administered over a period of time between five and thirty days. Suitable dosage ranges for other compounds can be readily determined by those of skill in the art.

In a preferred embodiment, the sustained release formulation includes naturally-occurring estradiol-17β which is microencapsulated into polylactide microspheres. The microspheres have excellent biocompatibility and naturally biodegrade into lactic acid over a period of several weeks, releasing physiologically useful levels of estradiol-17β during the above-described four to eleven day window to induce the pseudopregnancy, and releasing an effective amount of the compound to induce the pseudopregnancy.

The composition is preferably administered via intramuscular injection, preferably in the side of the neck. Intramuscular injections should be made by directing the needle into the fleshy part of the thick musculature of the neck, avoiding blood vessels and major nerves. Before injection, it is preferable to pull back gently on the plunger. If blood appears in the syringe, a blood vessel has been entered. The needle should be withdrawn and a different site should be selected. The injection site should be cleaned with a suitable disinfectant such as Betadine®.

B. Determination of Pseudopregnancy

Pseudopregnancy is measured by the presence of significantly prolonged (P<0.05) Inter Estrus Intervals (IEI) and the continued secretion of progesterone by the corpus lutea which blocks the normal return to estrus such as occurs in normal pregnancy. Progesterone concentrations greater than one ng/ml are indicative of the presence of corpus lutea.

C. Determination of Progesterone and Estradiol Concentrations

Progesterone and estradiol concentrations can be measured by bleeding the animal and analyzing the blood using standard detection methods such as HPLC or immunoassays.

Progesterone and estradiol concentrations can be measured in serum using a validated radioimmunoassay (RIA) for porcine samples as previously described by Stevenson et al., *Biol. Reprod.* 24: 341 (1981)) and Howard and Britt, *J. Reprod. Fert.* 90: 245 (1990), respectively.

D. Termination of Pseudopregnancy and Induction of Estrus

Termination of pseudopregnancy and induction of estrus can be achieved by administering an effective amount of PGF2α or its commercial analogs to the pseudopregnant gilts. Those of skill in the art can readily determine an effective amount of PGF2α or its analogs to administer to terminate the pseudopregnancy and induce estrus. One commercial formulation containing PGF2α which can be used to terminate the pseudopregnancy and induce estrus is known as Lutalyse™. A clinically effective dose of Lutalyse™ is about 10 mg dinoprost tromethamine/animal. Normal estrus with ovulation usually occurs between three and six days after injection. Preferably, a large number of pigs, preferably pseudopregnant gilts, are treated simultaneously so that the pigs will all return to estrus and be able to conceive at the same time. Once estrus has been simultaneously achieved in the pigs, they can be artificially inseminated simultaneously. Pregnancy in the swine can be detected using known methodology, for example, measurement of serum concentrations of progesterone and estradiol as described above with respect to determination of pseudopregnancy. In addition to gilts, sows can be treated, but they can also be controlled using weaning programs.

E. Determination of Estrus Behavior

Gilts can be checked for estrus by visual inspection. Based on the observed signs, the gilts can be classified as in estrus or not in estrus. Predominately positive estrus behavioral signs which are characteristic of estrus behavior for gilts are well known to those of skill in the art. Predominately negative or diestrus behavioral signs which are characteristic of diestrus behavior for gilts in general are also well known to those of skill in the art.

The present invention will be further understood with reference to the following non-limiting examples.

EXAMPLE 1

Regulation of Estrus and Ovulation in Gilts Using Estradiol Microspheres

Experimental Design

A controlled study was conducted to demonstrate that a single injection controlled release microsphere formulation could reliably induce pseudopregnancy following PG 600™ induced pubertal ovulations in 180 day old gilts. Four doses of estradiol microspheres were evaluated in this study. The study also demonstrated the effectiveness of Lutalyse™ (PGF 2α, 10 mg) to induce a controlled estrus in the pseudopregnant gilts at 59 days after treatment to induce luteolysis and estrus in a controlled manner.

The study was designed as a parallel group design. An equal number of gilts were randomized into the following treatment groups: placebo; polylactide microspheres containing: 12.5 mg Estradiol 17β; 25 mg Estradiol 17β; 50 mg Estradiol 17β; 100 mg Estradiol 17β.

To avoid interpretive bias, only study personnel uninvolved with experimental examinations prepared and administered the injections, as appropriate for each treatment group.

MATERIALS

Experimental Animals

All gilts met the following criteria prior to treatment:

1. They were prepubertal and between 160 and 200 days old prior to treatment with PG 600™ (Intervet Inc. Millsboro Del.); and 2. They responded to treatment with PG 600™ with a normal estrus three to six days following treatment.

Gilts exhibiting clinical reproductive abnormalities, gilts with infectious conditions and gilts receiving concurrent therapy were excluded. Gilts were managed under typical conditions prevailing in the commercial swine breeding industry and fed 1.8–2.7 $kg^{-1}$ of 14% crude protein corn/soybean diet fortified with vitamins and minerals to meet National Research Council recommendations (NRC, 1988).

Microparticle Formulation:

Poly(DL-lactide) microspheres containing estradiol 17-β (E2) were prepared using a solvent extraction process where a mixture of poly(DL-lactide) (Birmingham Polymers, Inc., Birmingham, Ala.), E2 and solvent were dispersed in water, and the solvent was subsequently removed to yield the desired microspheres. The microspheres were then collected by filtration, washed extensively with purified water and dried in a vacuum. The microspheres were characterized by core loading, SEM surface morphology and particle-size analysis after sterilization by exposure to gamma radiation.

A single injection controlled release formulation including these microspheres was used. Four different dosages of estradiol 17β were administered: 12.5 mg, 25 mg, 50 mg and 100 mg. Injection vehicle (0 mg estradiol 17β) was used as a placebo (0 mg group).

METHODS

Drug Packaging and Storage:

The drug was provided in sterile vials labeled in accordance with FDA regulations and was stored refrigerated (2°–8° C.) until use.

Preparation of Dosage

The sterile injection vehicle was warmed (not over 25° C.) before use. A sterile 16 or 18-gauge needle was inserted into a vial of sterile injection vehicle to release the vacuum. An empty syringe was attached to the needle, the vial containing the vehicle was inverted, and an appropriate volume of vehicle for each multi-dose vial was drawn out. The vehicle was injected into the vial containing the microspheres and needle was withdrawn. The vial was vigorously shaken for at least 1 minute to suspend the microspheres in the vehicle. After the microspheres were well dispersed, they were withdrawn into the syringe (approximately 1 ml for gilts receiving the 25, 50 or 100 mg estradiol dose and approximately 0.5 ml for gilts receiving the 12.5 mg dose). It was important that the microspheres were injected within two minutes of suspension to prevent the microspheres from settling out.

Intramuscular Injection:

The route of administration was by intramuscular injection in the side of the neck. Intramuscular injections were made by directing the needle into the fleshy part of the thick musculature of the neck, avoiding blood vessels and major nerves. Before injecting the suspension, the plunger was pulled back gently to determine whether a blood vessel was entered. In those cases where a blood vessel was entered, the needle was withdrawn and a different site selected.

Assessment of Response to Treatment

Determination of Estrous Behavior

Gilts were checked for estrus daily one or twice beginning day 18 after their first heat through day 22. Based on the observed signs the gilts were classified as in estrus (symbol E for estrus) if they exhibited predominately positive estrus behavioral signs which are characteristic of estrus behavior for gilts. Gilts not in estrus (symbol D for diestrus) exhibited predominately negative or diestrus behavioral signs which are characteristic of diestrus behavior for gilts. Gilts were also checked for estrus as described above following PGF2α treatment.

Determination of Pseudopregnancy

Pseudopregnancy is defined as gilts experiencing a significant ($P<0.05$) Inter Estrus Interval (IEI) and the continued secretion of progesterone by the corpus lutea. Progesterone concentrations greater than one ng/ml are considered to be indicative of the presence of corpus lutea. Maximal pseudopregnancy response is defined for purposes of this example only as gilts remaining pseudopregnant until day 59, the day at which Lutalyse™ was administered (i.e., an IEI greater than or equal to 59 days).

Determination of Progesterone and Estradiol Concentrations

Schedule for Sample Collection: All gilts were bled prior to estradiol treatment (day 14) and twice weekly until day 73 of the study.

Sample Handling: Sterile Vacutainer tubes (Becton-Dickinson) were used for collecting serum samples by jugular venipuncture. The tubes were labeled to identify the gilts, the date and the blood sample. Blood samples were allowed to clot overnight at 4° C. and serum collected by decanting the supernatant after centrifugation. Serum was stored at −20° C. until assayed for progesterone and estradiol.

Hormone Analysis: Progesterone and estradiol concentrations were measured in serum using a validated radioimmunoassay (RIA) for porcine samples as previously described by Stevenson et al. (Stevenson et al., "Biol. Reprod. 24: 341 (1981)) and Howard and Britt (Howard and Britt, J. Reprod. Fert. 90: 245 (1990)), respectively.

Analysis of Response to Treatment

The following criteria were evaluated to analyze the gilt's response to the treatment:

a) Corpus Lutea lifespan (as measured by monitoring progesterone concentrations);

b) Mammary score;

c) The percentage of gilts pseudopregnant at Day 59; and d) The percentage of pseudopregnant gilts responding to treatment with PGF2α on Day 59.

EXPERIMENTAL METHODS

Forty gilts 180 days old were induced to ovulate with PG600™ (Intervet Inc., Millsboro Del.) [Day 0]. Fourteen days later, gilts randomly received one of five blinded treatments (n=8/group). Treatments were 0 mg estradiol (E2) (vehicle) or 12.5, 25, 50, or 100 mg E2 in poly(DL-lactide) microspheres. Blood samples were collected prior to E2 treatment and twice weekly until day 73 to monitor progesterone (P4) and E2 concentrations.

On days 18 to 26, an intact boar was used to determine return to estrus. On day 59, gilts were injected with 10 mg $PGF_{2\alpha}$ and an intact boar was used to check estrus for seven days. On day 62, mammary development was scored (0=no development; 1=some development; 2=teat and gland development). Mammary score, Peak E2 concentrations and corpus luteum (CL) lifespan (P4>1 ng/ml) were analyzed using least squares ANOVA. The percentage of gilts with functional CL at 59 days and the percentage responding to $PGF_{2\alpha}$ treatment were analyzed using Chi-square analysis.

Results and Discussion

Statistical examination of the data presented in Table 1 strongly suggest the effectiveness of estradiol microspheres for stimulating pseudopregnancy based on continued CL P4 secretion greater than 1 ng/ml. E2 treatment also significantly stimulated mammary development in treated gilts at doses above 25 mg.

TABLE 1

E2 Microsphere Efficacy Data

| E2 Dose (mg) | CL Lifespan Days (SEM = 4) | Mammary Score (0 to 2) (SEM = 0.4) | Pseudo-Pregnant at 59 days % | Pseudo-Pregnancy Response to PCF % |
|---|---|---|---|---|
| 0 | 25[a] | 0[a] | 0%[a] | — |
| 12.5 | 46[b] | 0.6[a,b] | 50%[b] | 50% |
| 25 | 55[b] | 1.1[b] | 88%[b] | 71% |
| 50 | 51[b] | 1.4[b] | 86%[b] | 83% |
| 100 | 55[b] | 1.4[b] | 86%[b] | 100% |

Does not include 3 gilts that did not respond to PG600 ™;
[a,b]($P < .05$)

Serum concentrations of E2 were elevated ($p<0.05$) after treatment for ten to 30 days, depending on dose and peaked at 59, 1649, 3700, 4579, and 6635, pg/ml for the 0, 12.5, 25, 50, 100 mg groups respectively. The mean serum E2 levels are shown in FIG. 1.

Figure 2:
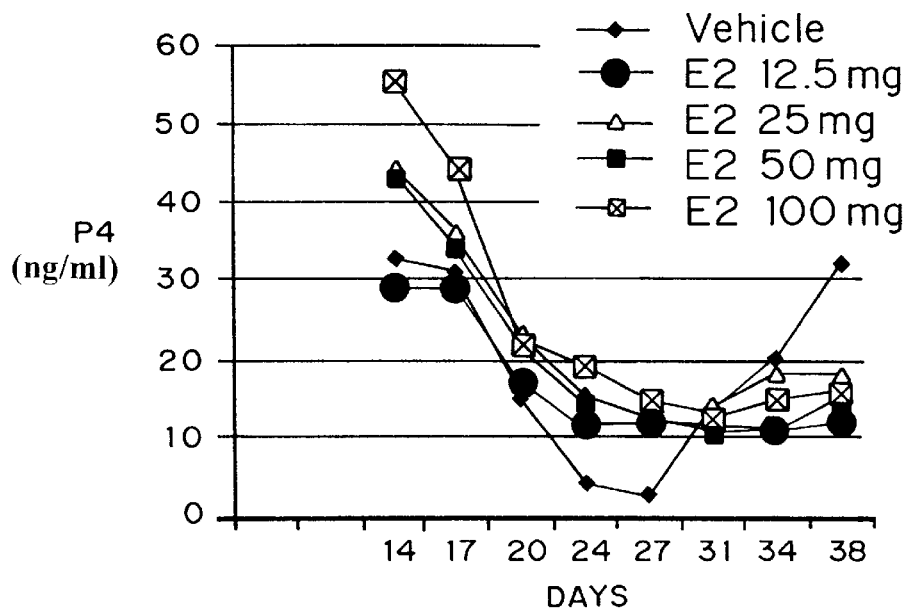
FIG. 2 is a graph showing the progesterone (P4) levels (pg/ml) in treated gilts. Filled diamonds represent vehicle. Circles represent treatment with 12.5 mg of estradiol. Triangles represent treatment with 25 mg of estradiol. Squares represent treatment with 50 mg of estradiol. Xs represent treatment with 100 mg of estradiol.

The mean serum P4 levels following E2 treatment, as shown in FIG. 2, remained elevated at luteal or pseudopregnant levels (P4 greater than 1 ng/ml) in all estradiol treatment groups for greater than 50 days. The data is statistically significant (p less than 0.05). This data confirms the effectiveness of the estradiol formulations for inducing pseudopregnancy.

Conclusion

A controlled release polylactide microsphere formulation designed to deliver estradiol 17β at physiologically useful levels over a period of time between 16 and 26 days was successful at inducing pseudopregnancy in gilts for greater than 50 days. Following induction of pseudopregnancy, the pseudopregnancy can be terminated and estrus induced by administration of a commercial analog of PGF2α. The advantages of inducing pseudopregnancy followed by induction of estrus are that the breeding patterns of large numbers of gilts can be controlled.

Modifications and variations of the compositions and methods described herein will be obvious to those skilled in the art from the foregoing detailed description. Such modifications and variations are intended to come within the scope of the appended claims.

We claim:

1. A method for inducing pseudopregnancy in fertile female pigs comprising administering to the pigs an effective amount of a compound that induces pseudopregnancy in a biodegradable controlled release formulation.

2. The method of claim 1 further comprising chemically inducing puberty in the gilts prior to induction of pseudopregnancy.

3. The method of claim 2 wherein the puberty was induced by administration of a combination of pregnant mare's serum gonadotrophin and human chorionic gonadotropin.

4. The method of claim 1 wherein the formulation comprises microparticles that release physiologically useful levels of the compound in a controlled fashion over a period of time between 5 and 30 days.

5. The method of claim 4 wherein the microparticles comprise a biodegradable polymer.

6. The method of claim 5 wherein the polymer is selected from the group consisting of polyhydroxy acids, polyorthoesters, polylactones, polycarbonates, polyphosphazenes, polysaccharides, proteins, polyanhydrides, copolymers thereof and blends thereof.

7. The method of claim 6 wherein the polymer is selected from the group consisting of polylactic acid, polyglycolic acid, and poly lactic-co-glycolic acid.

8. The method of claim 1 wherein the compound is selected from the group consisting of 17β-estradiol, mono esters of estradiol, diesters of estradiol, mono of estradiol, diethers of estradiol, alkyl derivatives at the 17 position of estradiol, conjugated equine estrogens, estrone, piperazine estrone sulfate, estriol, estriol succinate polyestrol phosphate, 17α-estradiol, and mixtures thereof.

9. The method of claim 1 wherein the compound is selected from the group consisting of estradiol, estrone, estriol, esters thereof and mixtures thereof.

10. The method of claim 1, further comprising administering a composition that induces estrus while the gilt or sow is pseudopregnant.

11. The method of claim 10 further comprising artificially inseminating the gilt or sow.

12. A composition for inducing pseudopregnancy in a gilt or sow comprising a biodegradable controlled release formulation of a compound that induces pseudopregnancy in a gilt or sow.

13. The composition of claim 12, wherein the formulation comprises microparticles.

14. The composition of claim 12 wherein the compound is selected from the group consisting of 17β-estradiol, mono esters of estradiol, diesters of estradiol, mono of estradiol, diethers of estradiol, alkyl derivatives at the 17 position of estradiol, conjugated equine estrogens, estrone, piperazine estrone sulfate, estriol, estriol succinate polyestrol phosphate, 17 α-estradiol and mixtures thereof.

15. The composition of claim 14 wherein the compound is selected from the group consisting of estradiol 17β, estrone, estriol, esters thereof and mixtures thereof.

16. The composition of claim 13 wherein the microparticles comprise a polymer selected from the group consisting of polyhydroxy acids, polyorthoesters, polylactones, polycarbonates, polyphosphazenes, polysaccharides, proteins, polyanhydrides, copolymers thereof and blends thereof.

17. The composition of claim 16 wherein the polymer is selected from the group consisting of polylactic acid, polyglycolic acid, and polylactic-co-glycolic acid.

18. The composition of claim 13 wherein the compound is estradiol 17β and the polymer is polylactic acid.

19. The method of claim 1 wherein the formulation comprises an in situ gelling system.

20. The method of claim 19 wherein the formulation comprises sucrose acetate isobutyrate.

21. The composition of claim 12 wherein the formulation comprises an in situ gelling system.

22. A method for inducing pseudopregnancy in fertile female pigs comprising administering to the pigs an effective amount of a compound that induces pseudopregnancy in an implantable controlled release formulation, which can be removed from the pigs following release of the compound.

23. A device for inducing pseudopregnancy in a gilt or sow comprising an implantable controlled release formulation of a compound that induces pseudopregnancy, wherein the device can be removed from the pigs following release of the compound.

24. The device of claim 23 wherein the formulation is selected from the group consisting of cervical rings, vaginal rings, sponges, and other intravaginal implants.

* * * * *